US 9,249,663 B2

United States Patent
Ma et al.

(10) Patent No.: US 9,249,663 B2
(45) Date of Patent: Feb. 2, 2016

(54) IMPACT RESISTANT LAGGING, METHOD FOR DESIGNING IMPACT RESISTANT LAGGING, AND APPARATUS FOR TESTING IMPACT RESISTANT LAGGING

(75) Inventors: Kevin Jinrong Ma, Cheswick, PA (US); John Stankus, Canonsburg, PA (US); Robert McGinnis, Butler, PA (US); Dakota Faulkner, Pittsburgh, PA (US); Demrey Brandon, Pittsburgh, PA (US); John Feyrer, Pittsburgh, PA (US)

(73) Assignee: FCI Holdings Delaware, Inc., Wilmington, DE (US)

( * ) Notice: Subject to any disclaimer, the term of this patent is extended or adjusted under 35 U.S.C. 154(b) by 760 days.

(21) Appl. No.: 12/714,139

(22) Filed: Feb. 26, 2010

(65) Prior Publication Data
US 2010/0266349 A1    Oct. 21, 2010

Related U.S. Application Data

(60) Provisional application No. 61/156,168, filed on Feb. 27, 2009.

(51) Int. Cl.
*E21D 11/18* (2006.01)
*E21D 11/28* (2006.01)

(52) U.S. Cl.
CPC ............... *E21D 11/18* (2013.01); *E21D 11/28* (2013.01)

(58) Field of Classification Search
CPC ..... E21D 15/04; E21D 15/502; E21D 11/155; E21D 11/18; E21D 15/02; E21D 15/14; E21D 15/50; E21D 23/04; E21D 11/152; E04B 1/3205; E04B 2001/1993
USPC ......... 405/272, 288; 52/403.1, 489.1, 586.05, 52/511, 177, 384, 385, 404, 561, 578, 52/782.1, 783.11, 783.19, 793.1, 794.1, 52/798.1
See application file for complete search history.

(56) References Cited

U.S. PATENT DOCUMENTS

| 16,767 | A | * | 3/1857 | Worthen | E04B 1/3205 52/459 |
|---|---|---|---|---|---|
| 25,537 | A | * | 9/1859 | Van Duzer | E01D 4/00 52/87 |
| 60,199 | A | * | 12/1866 | Lane | E04B 1/3205 522/270 |
| 396,824 | A | * | 1/1889 | Lorenz | E04F 19/061 524/459 |
| 701,034 | A | * | 5/1902 | Gray | E01F 5/005 405/124 |
| 708,463 | A | * | 9/1902 | Cheney | E04B 1/3205 52/174 |
| 855,160 | A | * | 5/1907 | Bush | E04D 13/08 454/166 |
| 1,350,493 | A | * | 8/1920 | Goodrich | E04B 1/3205 294/106 |

(Continued)

FOREIGN PATENT DOCUMENTS

EP    1452670 A1 *  9/2004
EP    2123839 A2 * 11/2009

*Primary Examiner* — Benjamin Fiorello
*Assistant Examiner* — Edwin Toledo-Duran
(74) *Attorney, Agent, or Firm* — The Webb Law Firm

(57) ABSTRACT

A steel set assembly includes a first pair of legs and a second pair of legs with the first pair of legs being spaced from and positioned opposite the second pair of legs. First and second beams are provided with the first beam being secured to one leg of the first pair of legs and one leg of the second pair of legs. The second beam is secured to the other leg of the first pair of legs and the other leg of the second pair of legs. A panel is secured to the first and second beams and includes a base having a top surface and a bottom surface, a block having a top surface and a bottom surface, and a pad. The block is secured to the base and the pad is positioned between the top surface of the base and the bottom surface of the block.

10 Claims, 12 Drawing Sheets

(56) References Cited

U.S. PATENT DOCUMENTS

| | | | | |
|---|---|---|---|---|
| 1,745,588 A * | 2/1930 | Shodron | E04B 1/3205 | 119/436 |
| 1,753,892 A * | 4/1930 | Wilhelm | E04B 7/105 | 52/478 |
| 1,854,241 A * | 4/1932 | Adams | E04B 2/62 | 52/489.1 |
| 1,889,770 A * | 12/1932 | Black | E04D 3/3605 | 52/489.1 |
| 1,973,742 A * | 9/1934 | Bruno | E01D 21/00 | 52/318 |
| 2,021,480 A * | 11/1935 | Louis | E04C 3/38 | 52/639 |
| 2,155,216 A * | 4/1939 | Palmer | E04B 1/3205 | 52/409 |
| 2,172,030 A * | 9/1939 | Whitley | E21D 11/10 | 405/150.2 |
| 2,232,845 A * | 2/1941 | Fieroh | E02D 7/02 | 175/416 |
| 2,287,370 A * | 6/1942 | Becker | E04B 7/08 | 52/261 |
| 2,292,078 A * | 8/1942 | Charles | E04B 1/342 | 135/116 |
| 2,360,285 A * | 10/1944 | Sherman | E04B 7/08 | 52/223.6 |
| 2,366,916 A * | 1/1945 | Le Tourneau | E01F 15/141 | 14/2.4 |
| 2,384,198 A * | 9/1945 | Sheldon | E04B 1/3205 | 52/461 |
| 2,612,854 A * | 10/1952 | Fuge | E04C 3/40 | 52/643 |
| 2,693,195 A * | 11/1954 | Frieder | E04B 1/34326 | 135/122 |
| 2,733,482 A * | 2/1956 | Doman | E04B 1/344 | 135/143 |
| 3,131,792 A * | 5/1964 | Groneman | A47F 11/02 | 138/157 |
| 3,146,864 A * | 9/1964 | Nystrom et al. | | 52/93.2 |
| 3,391,038 A * | 7/1968 | Whitesides | | 156/78 |
| 3,456,412 A * | 7/1969 | Decombas | E04D 3/3605 | 403/400 |
| 3,464,168 A * | 9/1969 | Lyons, Jr. | E04B 1/3205 | 52/223.7 |
| 3,466,832 A * | 9/1969 | March | E04B 7/107 | 52/262 |
| 3,505,765 A * | 4/1970 | Blaski | E04B 1/3205 | 52/630 |
| 3,511,011 A * | 5/1970 | Straus | E04D 3/30 | 52/478 |
| 3,524,666 A * | 8/1970 | Beach | B61D 17/10 | 403/279 |
| 3,535,836 A * | 10/1970 | Blaski | E04B 1/3205 | 52/80.1 |
| 3,604,492 A * | 9/1971 | Bayer | F16B 5/00 | 248/508 |
| 3,606,720 A * | 9/1971 | Cookson | E04D 3/30 | 52/478 |
| 3,611,649 A * | 10/1971 | Muller | E04B 7/14 | 52/14 |
| 3,686,805 A * | 8/1972 | Pofferi | E04F 19/06 | 52/220.3 |
| 3,703,794 A * | 11/1972 | Gracon | E04D 3/3601 | 24/347 |
| 3,797,189 A * | 3/1974 | Schnebel | E04D 3/06 | 52/479 |
| 3,940,892 A * | 3/1976 | Lindbergh | E04H 6/44 | 52/64 |
| 3,968,604 A * | 7/1976 | Hills | E04B 1/3205 | 52/745.07 |
| 3,984,956 A * | 10/1976 | Oger | E04B 1/3205 | 52/223.7 |
| 4,065,932 A * | 1/1978 | Oger | E21D 11/08 | 405/153 |
| 4,644,710 A * | 2/1987 | Lippe | E04B 1/3205 | 52/223.7 |
| 5,069,008 A * | 12/1991 | Ellen | E04B 7/102 | 52/309.11 |
| 5,159,790 A * | 11/1992 | Harding | E04B 1/3205 | 52/641 |
| 5,245,802 A * | 9/1993 | Davis | E04B 1/34315 | 135/97 |
| 5,308,196 A * | 5/1994 | Frederick | E21D 15/483 | 248/354.2 |
| 5,862,642 A * | 1/1999 | Erwin | E04H 17/1413 | 256/19 |
| 7,263,805 B2 * | 9/2007 | Chapus | E04H 3/165 | 135/906 |
| 7,305,798 B1 * | 12/2007 | Heierli | E04H 3/165 | 135/906 |
| 7,572,084 B2 * | 8/2009 | Robertson | E01F 5/005 | 14/24 |
| 7,673,425 B2 * | 3/2010 | Thomas | E04D 13/0445 | 52/177 |
| 2003/0041547 A1 * | 3/2003 | Gosselin | B27N 5/00 | 52/630 |
| 2003/0159370 A1 * | 8/2003 | Drew | E01D 4/00 | 52/561 |
| 2004/0134152 A1 * | 7/2004 | Powell | B28B 7/0088 | 52/561 |
| 2005/0229535 A1 * | 10/2005 | Garner | | |
| 2008/0115455 A1 * | 5/2008 | Nadon | E04B 1/3205 | 52/798.1 |
| 2008/0245007 A1 * | 10/2008 | McDonald | | 52/309.5 |
| 2010/0024334 A1 * | 2/2010 | Stanhope | E04B 1/84 | 52/281 |

* cited by examiner

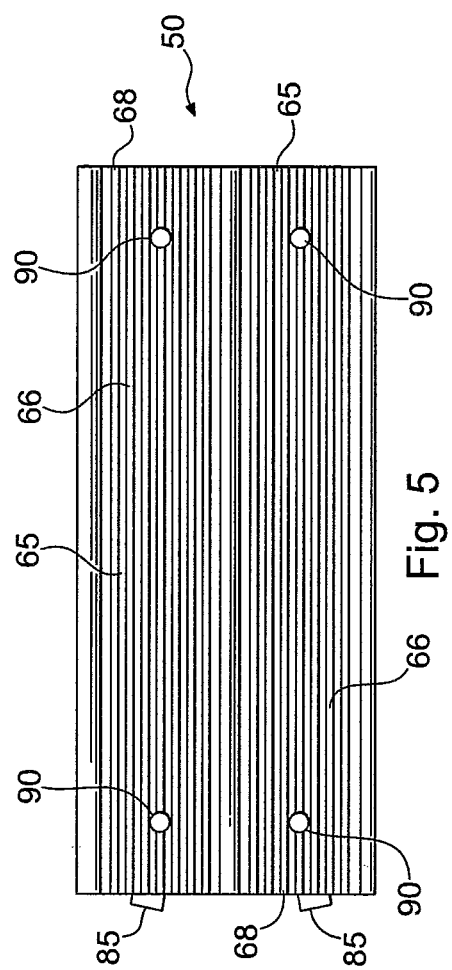
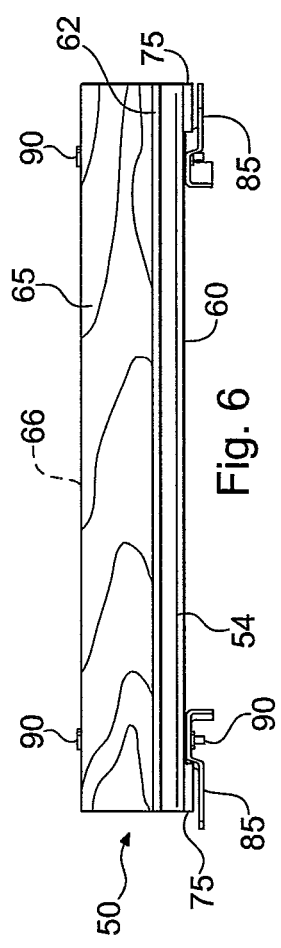

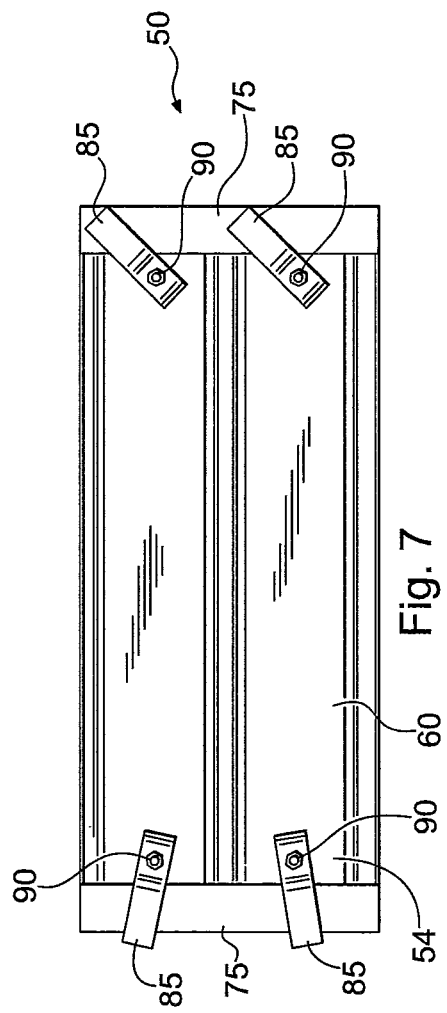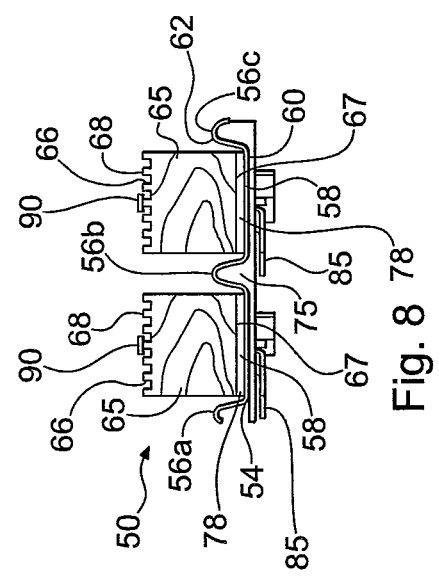

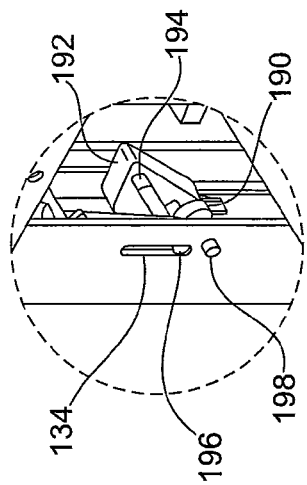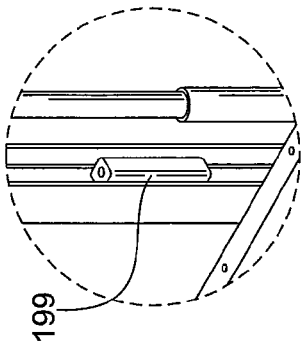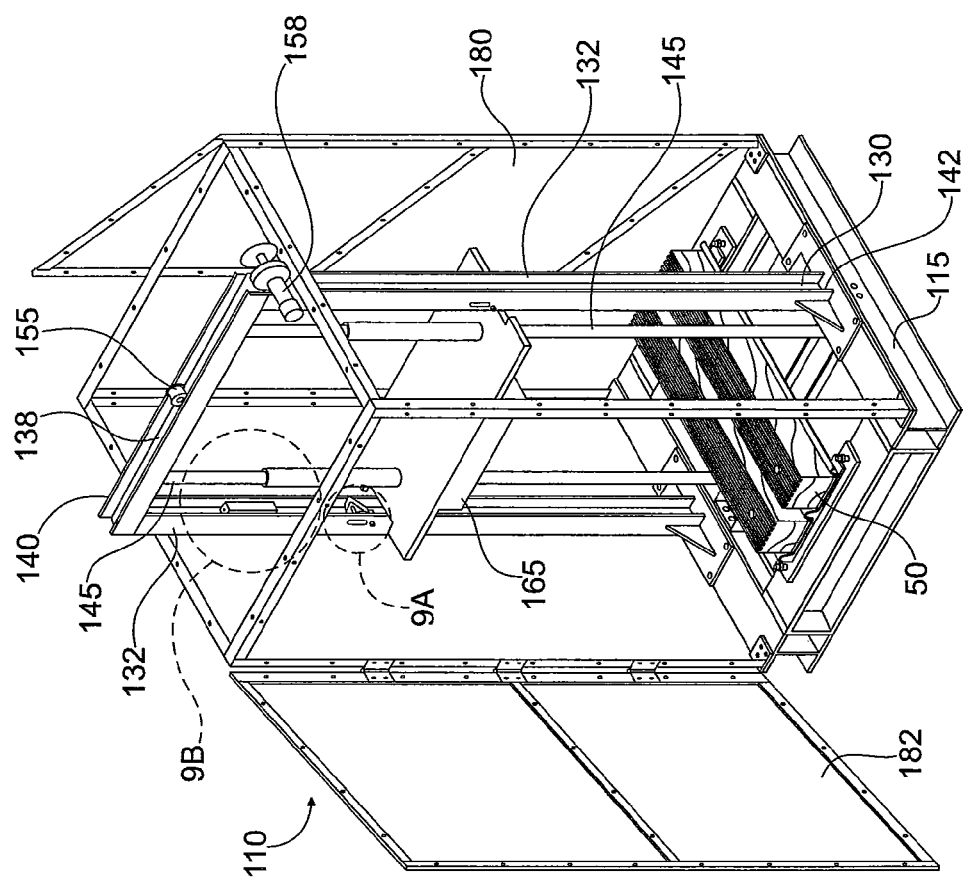

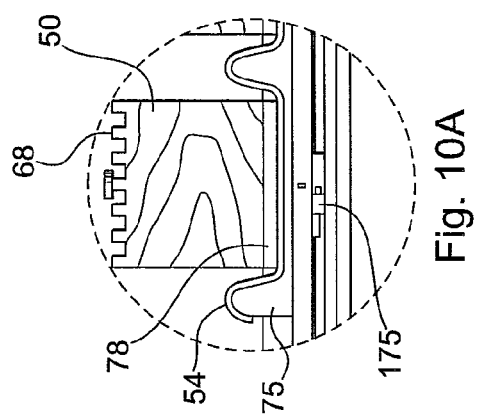
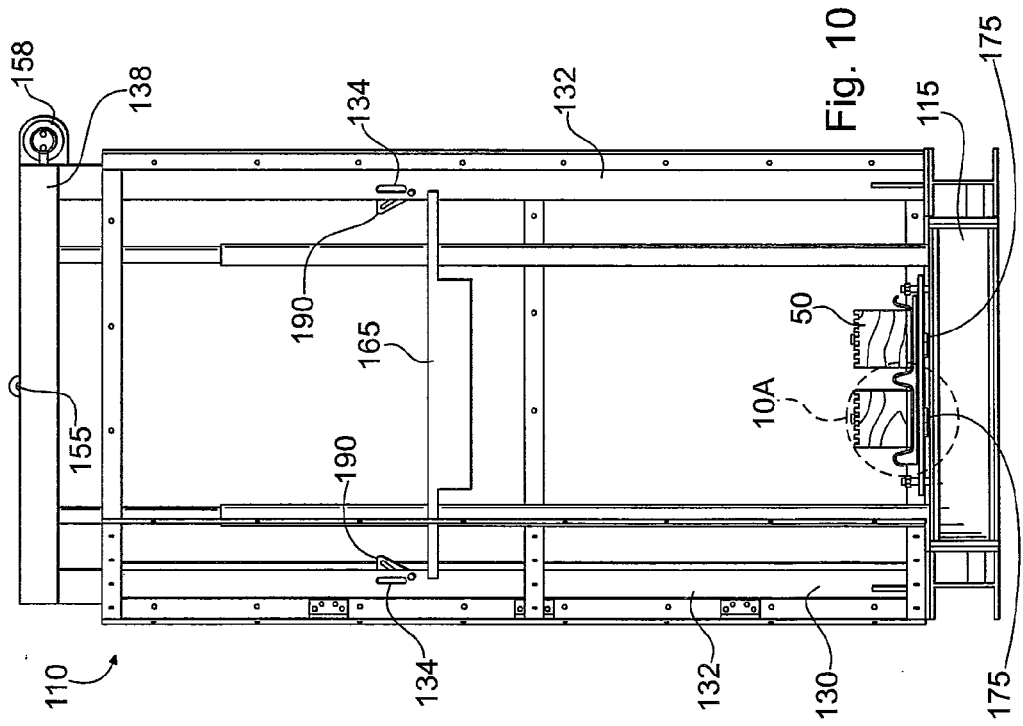

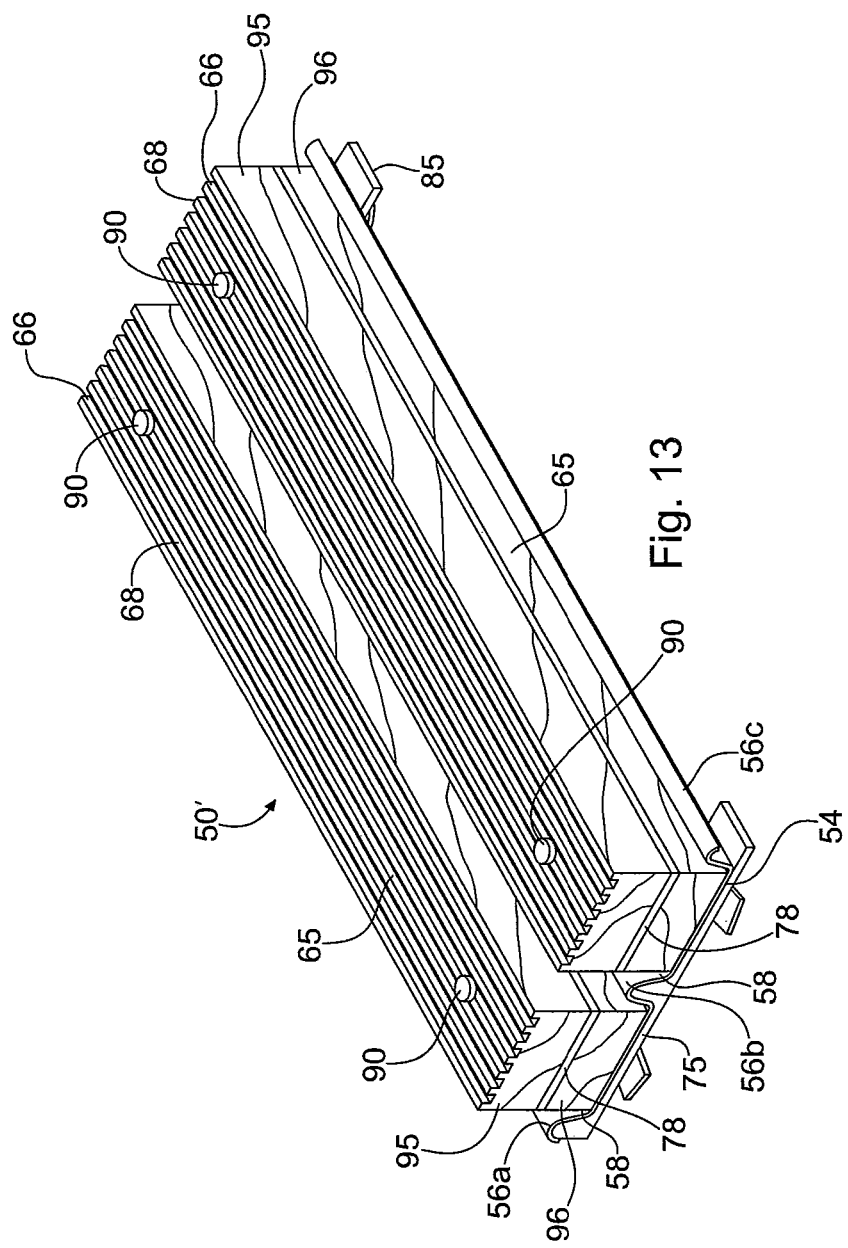

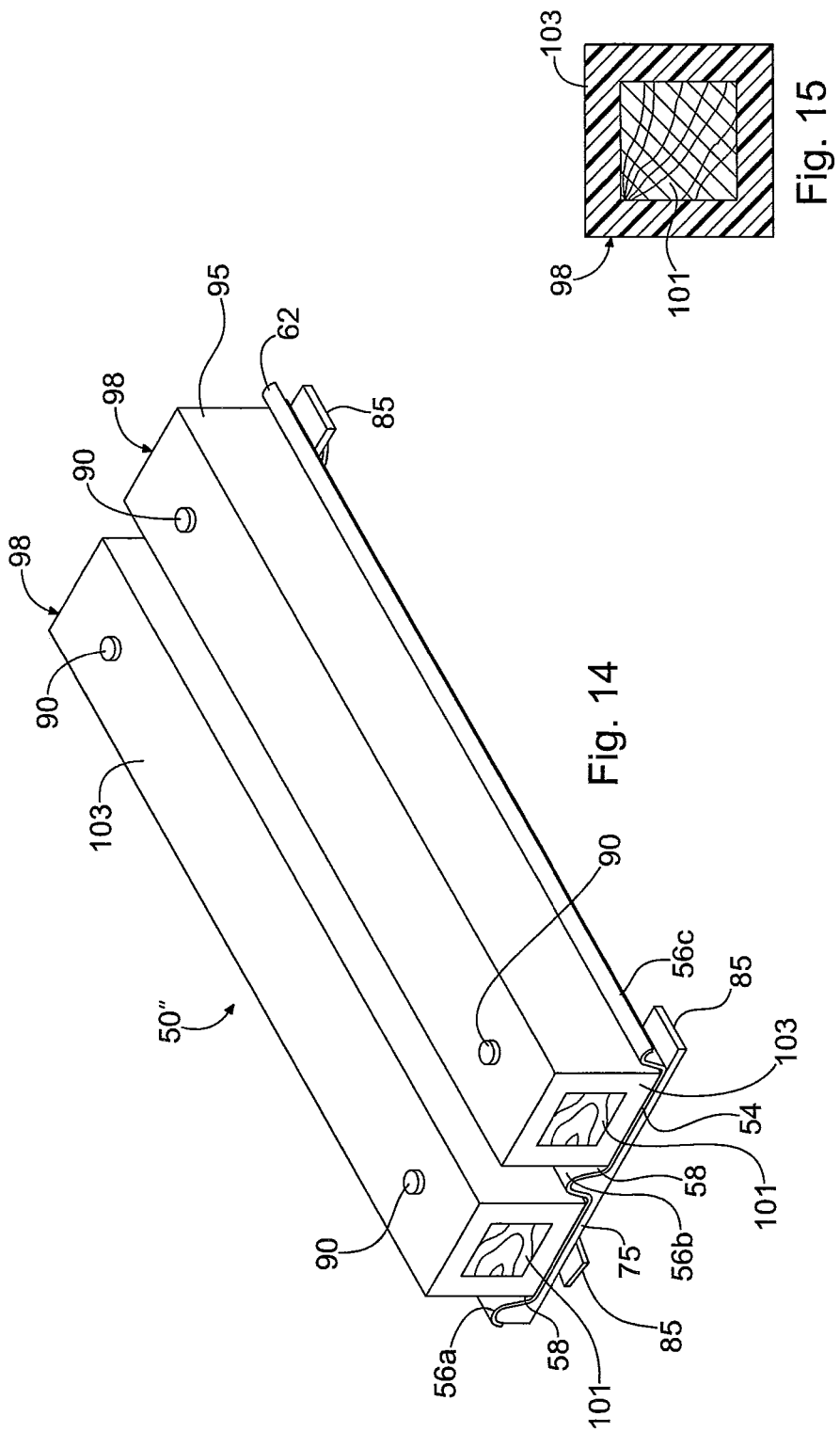

| Dropping height, ft | Weight, Lbs | Volume, ft^3 | Thickness, ft | Width, ft |
|---|---|---|---|---|
| 20 | 474.05 | 2.96 | 1.5 | 3.3 |
|  |  |  | 2 | 2.5 |
| 18 | 499.70 | 3.12 | 1.5 | 3.5 |
|  |  |  | 2 | 2.6 |
| 16 | 530.01 | 3.31 | 1.5 | 3.7 |
|  |  |  | 2 | 2.8 |
| 14 | 566.60 | 3.54 | 1.5 | 3.9 |
|  |  |  | 2 | 3.0 |
| 12 | 612.00 | 3.83 | 1.5 | 4.3 |
|  |  |  | 2 | 3.2 |
| 10 | 670.41 | 4.19 | 1.5 | 4.7 |
|  |  |  | 2 | 3.5 |
| 8 | 749.55 | 4.68 | 1.5 | 5.2 |
|  |  |  | 2 | 3.9 |
| 6 | 865.50 | 5.41 | 1.5 | 6.0 |
|  |  |  | 2 | 4.5 |
| 4 | 1060.02 | 6.63 | 1.5 | 7.4 |
|  |  |  | 2 | 5.5 |

Fig. 16

IMPACT RESISTANT LAGGING, METHOD FOR DESIGNING IMPACT RESISTANT LAGGING, AND APPARATUS FOR TESTING IMPACT RESISTANT LAGGING

CROSS-REFERENCE TO RELATED APPLICATION

This application claims the benefit of U.S. Provisional Application No. 61/156,168, filed Feb. 27, 2009, the entire content of which is hereby incorporated by reference.

BACKGROUND OF THE INVENTION

1. Field of the Invention

The present invention relates to underground mining and, more particularly, to lagging panels for roof control at underground openings.

2. Description of Related Art

Certain areas of underground openings are susceptible to a roof fall, i.e., falling rock, which presents a danger to mine personnel. Typically, when an underground opening has experienced a roof fall, the rock debris is removed from the area and the area of the roof fall is bolted and backfilled to reduce the risk of further rock fall. The process of bolting and backfilling the area of the roof that experienced roof fall, however, is a time consuming process that requires the mine to stop production. In addition, backfill material is costly and backfilling the large roof fall area can become prohibitively expensive. Accordingly, there is a need for a simple and reliable system to protect personnel and moving vehicles from falling rock.

Furthermore, there are currently no design guidelines and methodologies for lagging panels available that have been well-established to meet engineering needs in the underground mining industry. The design of lagging panels in the mining industry is generally based on trial-and-error and field experiences. Therefore, a practical and reliable lagging panel design methodology is needed which takes into account the impact loads the panel may be subjected to from the falling rock.

SUMMARY OF THE INVENTION

In one embodiment, a steel set assembly includes a first pair of legs and a second pair of legs with the first pair of legs being spaced from and positioned opposite the second pair of legs. The assembly also includes first and second beams and a panel secured to the first and second beams. The first beam is secured to one leg of the first pair of legs and one leg of the second pair of legs and the second beam is secured to the other leg of the first pair of legs and the other leg of the second pair of legs. The panel includes a base having a top surface and a bottom surface, a block having a top surface and a bottom surface, and a pad positioned between the top surface of the base and the bottom surface of the block with the block being secured to the base.

The base may define a plurality of raised portions and a receiving portion, where the receiving portion has a substantially planar surface and each raised portion extends from the substantially planar surface. The block may be positioned in the receiving portion. The panel may further include an insert positioned adjacent the bottom surface of the base with the insert conforming to the bottom surface of the base. The block may be a wood crib and the top surface of the block may define a plurality of grooves. The block may also include a core and an outer shell. The core may be wood and the outer shell may be plastic. The assembly may further include a plurality of clips secured to the bottom surface of the base with the clips securing the panel to the first and second beams. The assembly may also further include an insert positioned between the bottom surface of the base and at least one of the first and second beams.

In a further embodiment, a panel includes a base having a top surface and a bottom surface, a block having a top surface and a bottom surface, and a pad positioned between the top surface of the base and the bottom surface of the block with the block being secured to base.

The base may define a plurality of raised portions and a receiving portion with each raised portion extending from the top surface of the base and the receiving portion being defined between the raised portions. The block may be positioned in the receiving portion. The panel may further include an insert positioned adjacent the bottom surface of the base with the insert conforming to the bottom surface of the base. The block may be a wood crib and the top surface of the block may define a plurality of grooves. The panel may also further include a clip secured to the bottom surface of the base and an insert secured to the bottom surface of the base and positioned adjacent to the clip. A fastener may extend through the block, the pad, the base, and the clip.

In another embodiment, a testing apparatus includes a frame having a top end and a bottom end, a weight block movable between the top end and the bottom end, a guide member supported by the frame and receiving the weight block, and a protection mechanism having a stopper and an actuator. The stopper is operatively connected to the actuator and movable between an extended position and a retracted position. The stopper is configured to restrict the movement of the weight block when in the extended position.

The testing apparatus may further include a movable pin having a first position and a second position. The movable pin is received within a slot defined in the frame. The stopper may be pivotally connected to the frame via a pivot and may define a cam surface for receiving the movable pin. The actuator may be connected to the movable pin. The stopper may be in the retracted position when the movable pin is in the first position and the stopper may be in the extended position when the movable pin is in the second position. The testing apparatus may further include a base positioned adjacent the bottom end of the frame and a load cell positioned on the base.

BRIEF DESCRIPTION OF THE DRAWINGS

FIG. 5 is a top view of the impact resistant lagging panels shown in FIG. 1;

FIG. 6 is a side view of the impact resistant lagging panels shown in FIG. 1;

FIG. 7 is a bottom view of the impact resistant lagging panels shown in FIG. 1;

FIG. 8 is a front view of the impact resistant lagging panels shown in FIG. 1;

FIG. 9 is a perspective view of a testing apparatus for a lagging panel according to one embodiment of the present invention;

FIG. 9A is a detail view of the protection mechanism shown in FIG. 9;

FIG. 9B is a further detail view of the protection mechanism shown in FIG. 9;

FIG. 10 is a front view of the testing apparatus shown in FIG. 9;

FIG. 10A is a detail view of the load cell installed between impact resistant lagging panel and the base of the testing apparatus shown in FIG. 10;

FIG. 13 is a front top perspective view of an impact resistant lagging panel according to a further embodiment of the present invention;

FIG. 14 is a front top perspective view of an impact resistant lagging panels according to another embodiment of the present invention;

FIG. 15 is a cross-sectional view of a block shown in FIG. 14; and

FIG. 16 is a table of the size and height of falling rock that the lagging panel can withstand.

DESCRIPTION OF THE PREFERRED EMBODIMENTS

For the purposes of the description hereinafter, it is to be understood that the invention may assume various alternative variation step sequences, except where expressly specified to the contrary. It is also to be understood that the specific information illustrated in the attached drawings and described in the following specification are simply exemplary embodiments of the invention.

Figure 1:
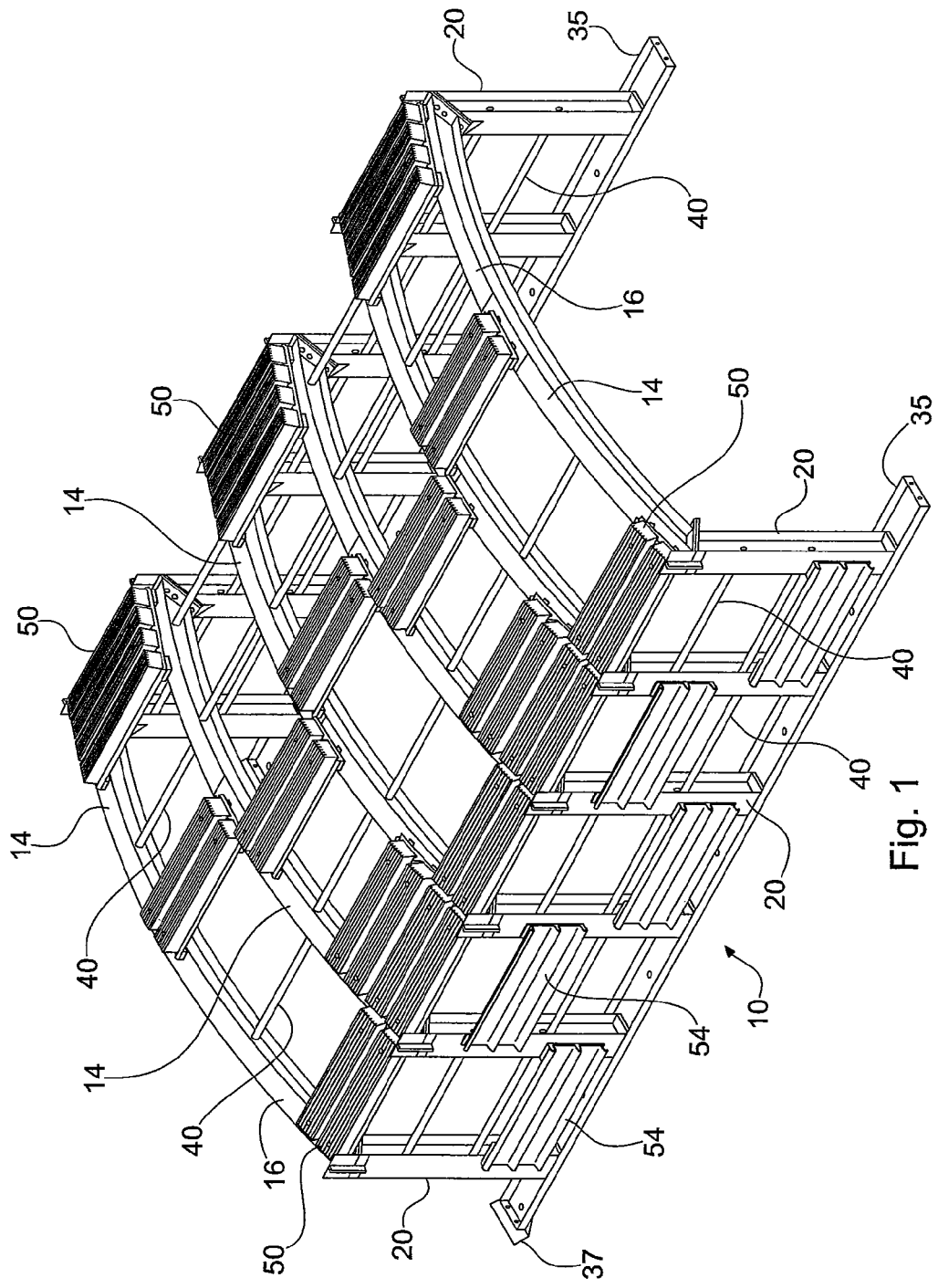
FIG. 1 is a perspective view of a steel set assembly with impact resistant lagging panels according to one embodiment of the present invention.
Figure 2:
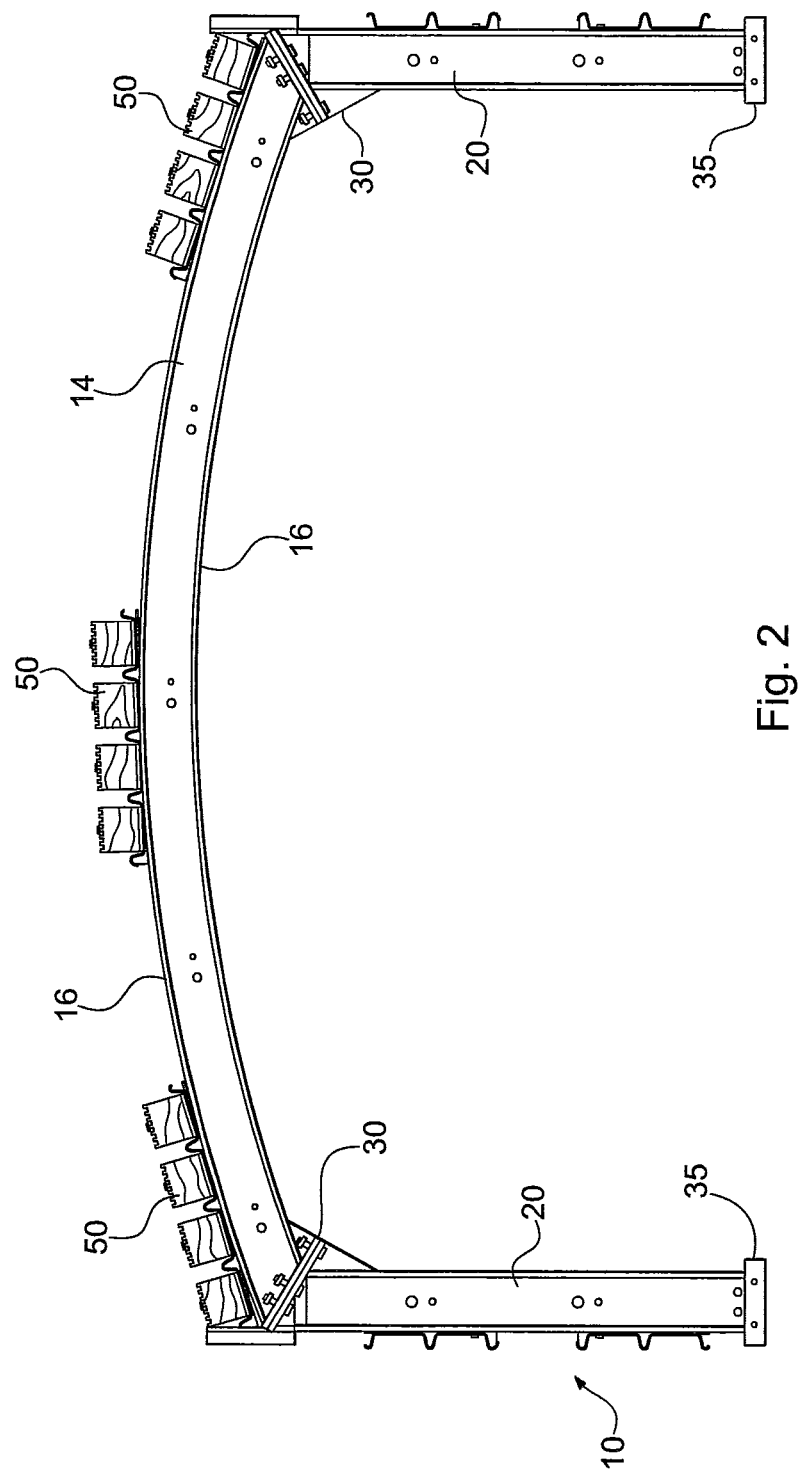
FIG. 2 is a front view of the steel set assembly with impact resistant lagging panels shown in FIG. 1.

Referring to FIGS. 1 and 2, one embodiment includes a three piece long radius arch set assembly 10 having a plurality of impact resistant lagging panels 50. The arch set assembly 10 includes beams 14 and legs 20 formed from W8×31 beams, although other types and sizes of support structure may be utilized to meet ground control requirements. The ends of each beam 14 are secured to the ends of respective legs 20, which are spaced from and positioned opposite each other, via a top connection plate and gusset 30 welded to the top of the leg 20 and bolted to the beam 14. The bottoms of the legs 20 are secured within a runner channel 35 via bolting, although other suitable securing arrangements for the bottoms of the legs may be provided. The runner channel 35 includes a runner skid 37 to enable easy sliding of the runner channel 35. Further, the arch set assembly 10 includes a tie rod and stabilizer pipe 40 positioned adjacent to beams 14 and legs 20. In particular, the tie rod and stabilizer pipes 40 extend perpendicularly between adjacent beams 14 and between adjacent legs 20. Although a three piece long radius arch set assembly 10 is disclosed, the steel set may be a square set, two piece arch set, or any other suitable steel set design. As discussed in more detail below, the impact resistant lagging panels 50 are secured to the arch set assembly 10 to provide protection from falling rock for personnel and moving vehicles positioned beneath the arch set assembly 10.

Figure 3:
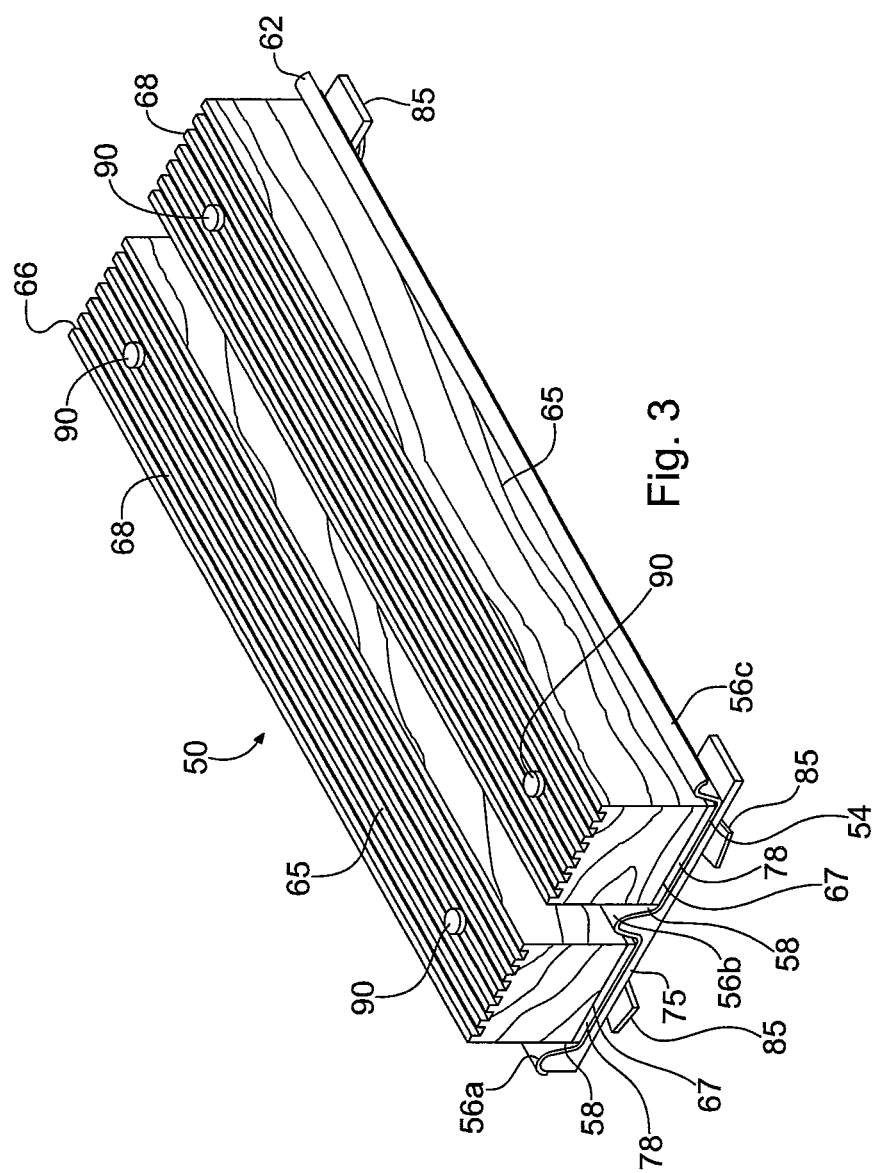
FIG. 3 is a front top perspective view of the impact resistant lagging panels shown in FIG. 1.
Figure 4:
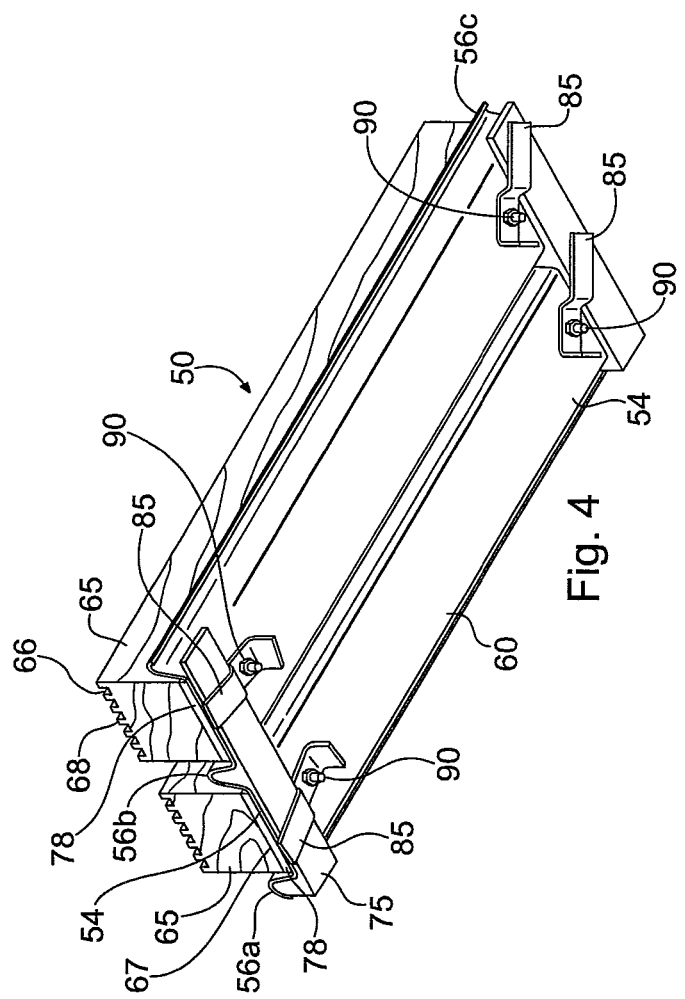
FIG. 4 is a front bottom perspective view of the impact resistant lagging panels shown in FIG. 1.
Figure 12:
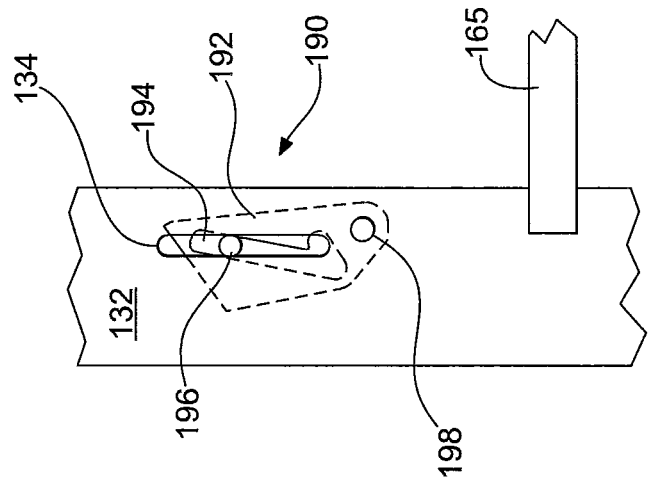
FIG. 12 is a side view of a weight protection mechanism of the testing apparatus of FIG. 9, showing the weight protection mechanism in a retracted position.
Figure 11:
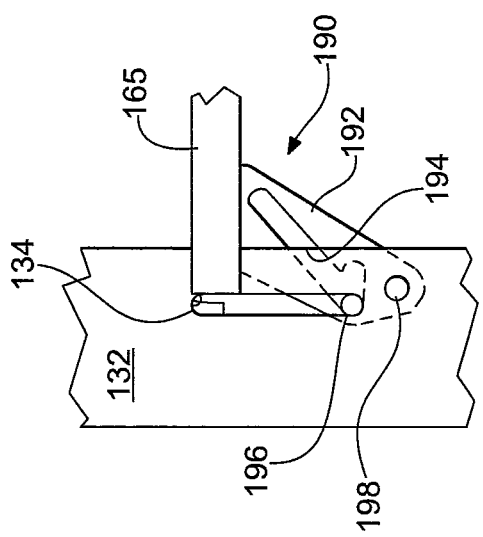
FIG. 11 is a side view of a weight protection mechanism of the testing apparatus of FIG. 9, showing the weight protection mechanism in an extended position.

Referring to FIGS. 3-8, in one embodiment, each impact resistant lagging panel 50 includes a base 54, a cushion pad 78, a cushion insert 75, a clip 85, and a fastener. In particular, as shown in FIGS. 3 and 4, for instance, each impact resistant lagging panel includes a base 54, two impact blocks 65, two cushion pads 78, two cushion inserts 75, four clips 85, and four fasteners 90, although other configurations and numbers of bases 54, blocks 65, pads 78, inserts 75, clips 85 and fasteners 90 may be utilized. The base 54 is a v-deck panel having raised portions 56a, 56b, 56c that extend the length of the base and define a receiving space 58 for the impact block 65, although other types of panels may be used for the base 54. The base 54 includes a bottom surface 60 and a top surface 62. The raised portions 56a, 56b, 56c of the base 54 extend from the substantially planar surface of the receiving space 58 and are generally v-shaped. Further, as shown more clearly in FIG. 8, the base 54 includes raised portions 56a, 56c positioned along the sides of the base 54 to allow lagging panels 50 that are positioned adjacent to each other to interlock via the raised portions 56a, 56c. In particular, the raised portion 56a of a first panel 50 may define a female connector to receive a male connector defined by the raised portion 56c of a second panel 50 positioned adjacent to the first panel 50 such that the upper surface of the raised portion 56c engages the underside of the raised portion 56a.

The impact block 65 includes a top surface 66 and a bottom surface 67 and is positioned in the receiving space 58 with the cushion pad 78 positioned between the top surface 62 of the base 54 and the bottom surface 67 of the impact block 65. The top surface 66 of the impact block 65 includes a grooved surface 68 to provide yieldability against impact, although the top surface 66 may also be smooth or include other surface configurations. The impact block 65 may be wooden, such as a wood crib, although other suitable materials may be used for the impact block 65. In particular, the material of the impact block 65 should having sufficient strength and ductility to withstand an impact from falling rock. As shown more clearly in FIG. 4, clips 85 are provided on the bottom surface 60 of the base 54 with the fasteners 90 extending through the impact block 65, base 54, and clips 85 to form an assembly. The clip 85 is rotatable about the fastener 90 prior to fully tightening the fastener 90. The cushion insert 75 is positioned adjacent the bottom surface 60 of the base 54. As shown in FIGS. 3 and 4, the cushion insert 75 conforms to the bottom surface 60 of the base 54, although the cushion insert 75 may have other shapes. The fastener 90 is a bolt and nut, although any other suitable fastening arrangement may be provided.

Referring again to FIGS. 1 and 2, the impact resistant lagging panels 50 are positioned on the arch set assembly 10, extending perpendicularly between adjacent beams 14. The impact resistant lagging panels 50 are shown to only extend between certain portions of beams 14 for the sake of clarity. In use, however, the panels 50 will typically be provided across the full length of the beams 14 such that there are no gaps or spaces for falling rock to pass through. The impact resistant lagging panels 50 are secured to a flange portion 16 of the beams 14 via the clips 85. In particular, the clips 85 may be rotated to allow the base 54 to sit flush on the beams 14 and may be subsequently rotated to be positioned beneath the flange 16 with the fasteners 90 being tightened to ensure that the lagging panel 50 is secured to the beam 14. When installed, the cushion insert 75 of the lagging panel 50 is positioned between the bottom surface 60 of the base 54 and the flange 16 of the beam 14. Further, as discussed above, the cushion pad 78 is positioned between the impact block 65 and the base 54. Accordingly, the cushion pad 78 and the cushion insert 75 are provided to absorb impact energy from falling rock striking the impact block 65. Further, as shown in FIG. 1, the base 54 alone may be positioned between adjacent legs 20 of the arch set assembly 10.

Referring to FIGS. 9 and 10, one embodiment of a testing apparatus 110 for lagging panels 50 is disclosed. The testing apparatus 110 includes a base 115, a frame 130, guide members 145, a pulley 155, a winch 158, a weight block 165, and dynamic load cells 175. The base 115 includes four beams arranged in a square-shaped structure. The frame 130 includes spaced-apart legs 132 secured to the base 115 with a top member 138 connecting the legs 132 to each other. The frame 130 has a top end 140 and a bottom end 142. The guide members 145 are positioned between the spaced-apart legs 132 of the frame 130 extending from the top end 140 to the bottom end 142 of the frame 130. In particular, the guide members 145 extend from the top member 138 towards the base 115. The guide members 145 may be a shaft constructed of pipe with an outer diameter that is smaller than the inner diameter of pipes that are welded to the weight block 165. The pulley 155 and winch 158 are positioned adjacent to the top member 138 of the frame 130. The weight block 165 is positioned between the spaced-apart legs 132 of the frame 130 with the guide members 145 extending through the weight block 165 such that the weight block 165 may be moved along the guide members 145. The weight block 165 is movable between the top end 140 and the bottom end 142 of the frame 130. The weight of the weight block 165 may be changed by adding or removing weights that are bolted to the weight block 165. A cable (not shown) is secured to the weight block 165 and is positioned through the pulley 155 for connection to the winch 158. A safety protection wall 180 with a door 182 is provided that surrounds the frame 130 and weight block 165. Further, a protection mechanism 190 is provided on the spaced-apart legs 132 of the frame 130. The safety protection wall 180 and the weight protection mechanism 190 will be discussed in more detail below.

During use of the testing apparatus 110, a testing sample, such as the impact resistant lagging panel 50 discussed above, is positioned on the base 115 so that the lagging panel 50 spans across the base 115. The span of the base 115 is designed to simulate the span between adjacent beams 14 of the arch set assembly 10 discussed above. The distance allows a determination of the actual impact forces the arch set assembly 10 will receive through the lagging panels 50. The dynamic load cells 175 are positioned between the lagging panel 50 and the base 115 of the testing apparatus 110. In particular, as shown more clearly in FIG. 10, the dynamic load cells 175 are positioned beneath each corner of the lagging panel 50 on the base 115. Prior to placing the lagging panel 50 for testing, the weight block 165 is raised along the guide members 145 using the winch 158. The weight block 165 is dropped by releasing the electronically-controlled winch 158 such that the weight block 165 free falls and impacts the lagging panel 50 positioned on the base 115. The readings from the dynamic load cells 175 may be recorded using a data acquisition system (not shown). The total impact force may be determined by taking the summation of the peak forces from the dynamic load cells 175. The weight block 165 may then be raised again so that the lagging panel 50 can be replaced for an additional test. The testing apparatus 110 consistently tests variations in the design of the lagging panels 50. In particular, the testing apparatus 110 consistently records the amount of instantaneous force that the lagging panel 50 is subjected to during a dynamic impact process. Through repeated testing of variations in design, the relative impact strength of each lagging panel 50 design can be determined.

Referring again to FIGS. 9 and 10, the testing apparatus 110 is surrounded by the safety protection wall 180 to shield personnel from flying debris caused by the impact of the weight block 165. Further, the protection wall 180 may be provided with two front and back split doors 182 that have sensors (not shown) to determine if they are closed and locked. In order for the weight block 165 to be raised, a control panel (not shown) will sense that the doors 182 are closed and locked. The doors 182 will be locked until the weight block 165 has reached the protection mechanism 190 or until the weight block 165 is in a lowered position. The protection wall 180 and the doors 182 may be constructed of plastic, such as polycarbonate, although other suitable materials may be used.

Referring to FIGS. 9-12, the protection mechanism 190, which is disposed between the spaced-apart legs 132 of the frame 130, includes a stopper 192 with a cam surface 194, a movable pin 196, a pivot 198, and an actuator 199. A protection mechanism 190 may be provided on each of the spaced-apart legs 132 of the frame 130. The pivot 198 is disposed through a bottom portion of the stopper 192 and secured to the leg 132 of the frame 130 such that the stopper 192 is pivotable about the pivot 198. The movable pin 196 is disposed through a slot 134 defined in the leg 132 of the frame 130. The cam surface 194 of the stopper 192 is configured to receive the movable pin 196. The movable pin 196 has a first position, shown in FIG. 12, and a second position, shown in FIG. 11. The actuator 199, which is shown more clearly in FIG. 9B, is operatively connected to the movable pin 196 to move the pin 196 within the slot 134 of the leg 132 between the first and second position. The stopper 192 has an extended position, shown in FIG. 11, and a retracted position, shown in FIG. 12. In the extended position, the actuator 199 moves the movable pin 196 to the second position toward the bottom of the slot 134 in the leg 132, which, due to the arrangement of the cam surface 194 of the stopper 192, extends the stopper 192 from the leg 132. In the retracted position, the actuator 199 moves the movable pin 196 to the first position toward the top of the slot 134 in the leg 132, which, due to the arrangement of the cam surface 194 of the stopper 192, retracts the stopper 192 to a position within the leg 132 of the frame 130. In other words, when the movable pin 196 is moved from the first position to the second position, the movable pin 196 engages the cam surface 194 of the stopper 192 thereby pivoting the stopper 192 about the pivot 198. When the weight block 165 is in a raised position, the stopper 192 of the protection mechanism 190 may be placed in the extended position such that the weight block 165 rests on the stopper 192. In case of a power failure and release of the winch 158, the weight block 165 will be supported by the weight protection mechanism 190 thereby preventing possible injury to personnel positioned beneath the weight block 165. When the weight block 165 is raised and hits the stopper 192, the cam surface 194 of the stopper 192 allows the stopper to rotate out of the way then spring back once the weight block 165 slides by. The weight protection mechanism 190 will only be disengaged when the operator is ready to drop the weight block 165.

Referring to FIG. 13, a further embodiment of an impact resistant lagging panel 50' is disclosed. The impact resistant lagging panel 50' is substantially similar to the lagging panel 50 described above and may be used similarly in arch set assembly 10, except each impact block 65 is provided as a top block 95 and a bottom block 96 with the cushion pad 78 positioned between the top and bottom blocks 95, 96. The cushion pad 78 provides further impact absorption for the lagging panel 50'.

Referring to FIGS. 14 and 15, another embodiment of an impact resistant lagging panel 50" is disclosed. The impact resistant lagging panel 50" is substantially similar to the lagging panel 50 described above and may be used similarly in arch set assembly 10. Rather than being provided with the impact block 65 described above, however, the panel 50" includes an impact block 98 having a core 101 with an outer shell 103. The core 101 may be formed from wood or steel and the outer shell may be formed from a composite plastic. In a particular embodiment, the core 101 is formed from treated hard wood and the outer shell 103 is formed from soft to medium soft recycled rubber or recycled plastic. The outer shell 103 may be substantially impermeable to moisture. In certain embodiments, the outer shell 103 is formed from a composite plastic material commercially available from IntegriCo Composites located at 4310 Lucius McCelvey Drive, Temple, Tex. 76504. The ends of the block 98 are shown having a portion of the core 101 being exposed, but the outer shell 103 may be provided such that the shell 103 completely encompasses the core 101. It has been found that the block 98 having plastic shell 103 exhibits enhanced durability (particularly moisture resistance), impact resistance, and strength as compared to blocks not having a plastic shell. In one non-limiting embodiment, the core 101 is sized about 3.5 inches by 3.5 inches and the shell 103 is about 1 to 2 inches thick. Although the impact resistant lagging panel 50" does not include the pad 78 of the panel 50 described above, the panel 50" may also include the pad 78. In addition, core 101 within block 98 may be provided with a grooved surface (not shown) as in block 65. The outer surface of the outer shell 103 may also be provided with a grooved surface (not shown) as in block 65.

In a further embodiment, a method of designing an impact resistant lagging panel is disclosed. The method includes: a) estimating the size of falling rock and roof fall height; b) applying impulse-momentum theory based on values obtained in step a) to obtain an impact load value; and c) designing a lagging panel based on the impact load value. The method may also include the step of fabricating a lagging panel based on the design obtained in step c).

The size of the falling rock and the roof fall height may be estimated based upon an evaluation of rock strata and roof condition. The condition of the rock strata may be determined based on core samples previously taken as well as information known to mine operators through experience of operating in a particular area. For instance, if the immediate roof is known to be thinly laminated, the rocks from a secondary roof fall will generally be small in size. The size of falling rock and roof fall height may also be estimated based on previous roof falls in the area.

Once the size and height of the falling rock is estimated, the impulse-momentum theory may be applied. The impulse-momentum theory is described by the following equations:

$$P\Delta t = M(V_f - V_i) \quad \text{(Equation 1)}$$

$$M = (w) \times (t) \times (s) \times (\gamma) \quad \text{(Equation 2)}$$

$$V_i = \sqrt{2gH} \quad \text{(Equation 3)}$$

P is the impact load;
$\Delta t$ is the duration of impact;
M is the mass;
w is the width of the falling rock;
t is the thickness of the falling rock;
s is the unit length of the rock layer (s=1);
$\gamma$ is the average density of fractured rock (assuming 120 lb/ft$^3$ or other appropriate value);
$V_i$ is the velocity of the falling rock before impact;
H is the falling height;
g is the gravitational acceleration;
$V_f$ is the velocity of falling rock after impact (assuming 0).

The size of the falling rock, i.e., the width (w) and thickness (t), is obtained from the estimation in the previous step. The falling height (H) is also obtained from the estimation in the previous step. Thus, the mass (M) and the velocity of the falling rock before impact ($V_i$) can be calculated using Equations 2 and 3. Although the average density of the fractured rock ($\gamma$) was assumed to be 120 lb/ft$^3$, other appropriate values may be used. The duration of the impact ($\Delta t$) is dependent on the properties of the lagging panel 50 being impacted. For instance, the ductility of the impact block and the amount and type of cushioning used in the lagging panel 50 will affect the duration of the impact ($\Delta t$). The duration of the impact ($\Delta t$) for a particular lagging panel arrangement may be determined through laboratory testing, which will be discussed below in more detail. Because the rest of the values are now known, the impact load (P) may then be determined using Equation 1. Based upon the impact load (P) value, a lagging panel 50 may be designed to withstand the impact from falling rock.

The method may further include the step of performing finite element computer modeling to determine the dynamic impact support capacity of a particular lagging panel. The impact resistant lagging panel 50, which was discussed above, was modeled to determine the dynamic impact support capacity assuming the lagging panel 50 is supported over a 4 foot span by W8×31 beams on both ends. The vertical deformation and safety factor distribution of the impact resistant lagging panel 50 at the given impact load (P) are determined from the computer model. More specifically, with 68 kips of impact load (P) at the mid-span, the supported beam develops less than 0.16" deflection at the mid-span, and material yielding initiates at the outmost fiber at the bottom of the V-deck panel and at the top of the wood cribs. Since the lagging panel 50 deflects within the serviceability range (typically 1/360 span) and the yielding zone does not propagate thru the impact blocks, it can be concluded that the lagging panel 50 has adequate strength to sustain 68 kips of dynamic impact load (P). If the design of the lagging panel 50 is determined to be insufficient from the computer modeling, the design of the panel 50 may be modified by altering the size of the components, selecting alternative materials, or making other suitable changes to the design to ensure the panel can sustain the estimated impact loads. The design process may be repeated to select a design that has a suitable dynamic impact support capacity. Accordingly, finite element computer modeling may be used to design a lagging panel 50 to withstand the impact load (P) determined using Equation 1.

The peak impact load (P) and the duration of the impact may be determined by conducting a test using the testing apparatus 110 shown in FIGS. 9 and 10 and discussed in more detail above. To simulate the actual loading condition, the weight block 165 falls down freely at a height of approximately 7' above the lagging panel 50. The weight block 165 may weigh 500 to 1000 lbs. The four dynamic load cells 175 are positioned underneath the lagging panel 50 and a computerized data acquisition system identifies instantaneous peak impact load (P) and duration of impact. The tests may be conducted using different lagging panel 50 configurations. Through the testing, the duration of impact of the impact resistant lagging panel was determined to be approximately 0.25 second, which was an increase in the duration of time of impact over other lagging panel configurations without the impact block 65 and cushions 75, 78. Thus, the impact resistant capacity of the impact resistant lagging panel 50 was dramatically increased.

Based on the laboratory testing and finite element analysis of the lagging panel 50, a maximum impact load the panel can sustain without failure is determined. Referring to FIG. 16, a table can be compiled showing various sizes of falling rock for different falling heights, which represent the maximum values (height and size of falling rock) that the lagging panel 50 can sustain. The values in the table are provided assuming the lagging panel 50 can sustain 68 kips of impact load (P) within 0.25 second duration. The table may be used to determine if the lagging system will be destroyed by falling rock by making a visual estimate of possible size and height of the falling rock in the field. For example, the impact resistant lagging panel can sustain an instantaneous load generated by a maximum 2' thick, 2.5° wide rock layer falling at a 20' height from the top of the arch set.

The above invention has been described with reference to the preferred embodiments. Obvious modifications, combinations and alterations will occur to others upon reading the preceding detailed description. Accordingly, the foregoing description is intended to be illustrative rather than restrictive.

The invention claimed is:

1. A steel set assembly comprising:
    a first pair of legs and a second pair of legs, the first pair of legs being spaced from and positioned opposite the second pair of legs;
    first and second beams, the first beam secured to one leg of the first pair of legs and one leg of the second pair of legs, the second beam secured to the other leg of the first pair of legs and the other leg of the second pair of legs;
    a plurality of tie rods, each of the plurality of tie rods extending between the first and second beams; and
    a panel assembly secured to the first and second beams, the panel assembly comprising:
        a base having a top surface and a bottom surface, the base defining a plurality of raised portions and a plurality of receiving portions, each of the plurality of receiving portions having a substantially planar surface, each of the plurality of raised portions extending from the respective substantially planar surfaces; and
        a plurality of blocks, each of the plurality of blocks having a top surface and a bottom surface, each of the plurality of blocks being secured to the base and positioned in one of the plurality of receiving portions, wherein the base extends between the first and second beams and is secured to the first and second beams, each of the plurality of blocks positioned adjacent to another one of the plurality of blocks, each of the plurality of blocks extending between the first and second beams, the top surface of each block is configured to provide protection from falling rock to a space beneath the first and second beams, wherein the steel set assembly is configured to be placed in an underground mine opening.

2. The steel assembly of claim 1, further comprising an insert positioned adjacent the bottom surface of the base, the insert conforming to the bottom surface of the base.

3. The steel set assembly of claim 1, further comprising an insert positioned adjacent the bottom surface of the base.

4. The steel set assembly of claim 1, wherein each block comprises a wood crib.

5. The steel set assembly of claim 4, wherein the top surface of each of the plurality of blocks defines a plurality of grooves.

6. The steel set assembly of claim 1, wherein the top surface of each of the plurality of blocks defines a plurality of grooves.

7. The steel set assembly of claim 1, further comprising a plurality of clips secured to the bottom surface of the base, the clips securing the panel to the first and second beams.

8. The steel set assembly of claim 7, further comprising an insert positioned between the bottom surface of the base and at least one of the first and second beams.

9. The steel set assembly of claim 8, wherein a fastener extends through each of the plurality of blocks, the base, and the clip.

10. The steel set assembly of claim 1, wherein each of the plurality of blocks comprises a core and an outer shell.

* * * * *